United States Patent [19]

Ayres et al.

[11] Patent Number: 5,635,484
[45] Date of Patent: Jun. 3, 1997

[54] PROPIONIBACTERIA PEPTIDE MICROCIN

[75] Inventors: James W. Ayres; William E. Sandine, both of Corvallis; George H. Weber, Portland, all of Oreg.

[73] Assignee: The State of Oregon Acting by and through the Oregon State Board of Higher Education on Behalf of Oregon State University, Eugene, Oreg.

[21] Appl. No.: 150,490

[22] Filed: Nov. 9, 1993

Related U.S. Application Data

[63] Continuation-in-part of Ser. No. 852,292, Mar. 16, 1992, Pat. No. 5,260,061, which is a continuation-in-part of Ser. No. 192,231, May 9, 1988, Pat. No. 5,096,718, which is a continuation-in-part of Ser. No. 753,563, Jul. 10, 1985, abandoned, which is a continuation-in-part of Ser. No. 419,559, Sep. 17, 1982, abandoned.

[51] Int. Cl.$^6$ .............. A61K 38/00; C07K 5/00; C07K 7/00; C07K 17/00
[52] U.S. Cl. .............. 514/18; 514/19; 530/331; 530/330; 562/559
[58] Field of Search .............. 530/300, 331; 514/18, 19; 562/559; 526/575; 426/532

[56] References Cited

U.S. PATENT DOCUMENTS

| | | | |
|---|---|---|---|
| 1,449,959 | 3/1923 | Staude | 435/42 |
| 1,470,885 | 10/1923 | Sherman et al. | 435/141 |
| 1,910,130 | 5/1933 | Sherman | 435/141 |
| 1,937,672 | 12/1933 | Sherman | 435/141 |
| 2,154,499 | 4/1939 | Elsenstein | 433/219 |
| 2,465,905 | 3/1949 | Meade et al. | 426/41 |
| 3,404,987 | 10/1968 | Kooistra et al. | 426/9 |
| 3,681,091 | 8/1972 | Kohl et al. | 426/532 |
| 3,779,796 | 12/1973 | Ueno et al. | 562/606 |
| 3,812,269 | 5/1974 | Mueller et al. | 426/227 |
| 3,846,567 | 11/1974 | Matyas et al. | 426/289 |
| 3,895,116 | 7/1975 | Herting et al. | 424/317 |
| 3,928,620 | 12/1975 | Courtade et al. | 424/317 |
| 4,199,606 | 4/1980 | Bland | 426/331 |
| 4,308,293 | 12/1981 | Tribble et al. | 426/532 |
| 4,497,833 | 2/1985 | Anderson | 426/41 |
| 4,728,516 | 3/1988 | Boudreaux et al. | 426/38 |
| 4,806,368 | 2/1989 | Reddy | 426/61 |
| 4,981,705 | 1/1991 | Tomes | 426/53 |
| 5,096,718 | 3/1992 | Ayres et al. | 426/9 |
| 5,260,061 | 11/1993 | Ayres et al. | 424/115 |

FOREIGN PATENT DOCUMENTS

| | | |
|---|---|---|
| 618210 | 4/1961 | Canada . |
| 1061632 | 9/1979 | Canada . |
| 1218894 | 2/1992 | Canada . |
| 2048977 | 2/1992 | Canada . |
| 0095268 | 11/1983 | European Pat. Off. . |
| 0096477 | 12/1983 | European Pat. Off. . |
| 233566 | 8/1987 | European Pat. Off. . |
| 1321702 | 6/1973 | United Kingdom . |
| 1420237 | 1/1976 | United Kingdom . |
| 2060346 | 5/1981 | United Kingdom . |

OTHER PUBLICATIONS

Bhunia et al., "Direct Detection of an Antimicrobial Peptide of *Pediococcus aidilactici* in Sodium Dodecyl Sulfate–Polyacrylamide Gel Electrophoresis," *J. Indust. Microbiol.* 2:1b–4b (1987).

Chung et al., "Growth of Salmonella at Low pH," *J. Food Sci.*, 35:326 (1970).

*The Condensed Chemical Dictionary*, 10th ed., UNR, N.Y. p. 862 (1981).

Hettinga et al., "Pouch Method for Isolating and Enumerating Propionibacteria," *J. Dairy Sci.* 51:1707–1709 (1968).

Hettinga et al., "The Propionic–Acid Bacteria—A Review," *J. Milk Food Technol.* 35:295–301, 358–372, 436–447 (1972).

Ingle, "Some Preliminary Observations on the Effectiveness of Propionates as Mold Inhibitors on Dairy Products," *J. Dairy Sci.* 23:509 (1940).

Isshiki et al., "Preservatives and Artificial Sweetners," *J. Assoc. Off. Anal. Chem.* 64:280–281 (1981).

Jackel et al., "A New Dried Dairy Culture Ingredient for Bakers," *The Bakers Digest* 6:38–39 (1975).

Jennes et al., *Principles of Dairy Chemistry*, Chapman & Hall, N.Y. 370–375 (1959).

Johnston et al., "Incidence of Salmonella in Fresh Pork Sausage in 1979 Compared with 1969," *J. Food Sci.* 47:1369–1371 (1982).

Kishishita et al., "New Medium for Isolating Propionibacteria and Its Application to Assay of Normal Flora of Human Facial Skin," *App. & Env. Microbiol.* 10:1100–1105 (1980).

Koshikowski, *Cheese and Fermented Milk Foods*, pub'd by author, Ithaca, N.Y. 12, 15, 47–49, 235–330 (1966).

Kriek et al., "Toxicity of *Pencillium Italicum* to Laboratory Animals," *Fd. Cosmet. Toxicol.* 19:311–315 (1981).

Langsrud et al., "Flavor Development and Microbiology of Swiss Cheese—A Review: I. Milk Quality and Treatments," *J. Milk Food Technol.* 36:487–490 (1973).

Langsrud et al., "Flavor Development and Microbiology of Swiss Cheese—A Review: II. Starters, Manufacturing Processes and Procedures," *J. Milk Food Technol.* 36:531–542 (1973).

Langsrud et al., "Flavor Development and Microbiology of Swiss Cheese—A Reivew: III. Ripening and Flavor Production," *J. Milk Food Technol.* 36:593–609 (1973).

Langsrud et al., "Flavor Development and Microbiology of Swiss Cheese—A Review: IV. Defects," *J. Milk Food Technol.* 37:26–41 (1974).

Lindsay et al., "Identification of Volatile Flavor Components of Butter Culture," *Jour. Diary Sci.* 43:1566–1574 (1965).

Malik et al., "An Evaluation of the Taxonomy of Propionibacterium," *Canadian J. Microbiol.* 14:1185–1191 (1968).

Marsili et al., "High Performance Liquid Chromatographic Determination of Organic Acids in Dairy Products," *J. Food Sci.* 46:52–57 (1981).

*The Merck Index*, 9th ed., p. 7614 (1976).

Miller, "Mold Growth on Cheddar Cheese and Its Control," *Preceedings, Institute of Food Technol.* 1:153–158 (1940).

Nieuwenhof, "Stimulating Effect of Lactobacilli on the Growth of Propionibacteria in Cheese," *Neth. Milk Dairy J.* 23:287–289 (1969).

Reynolds et al., "Bactericidal Properties of Acetic and Propionic Acids on Pork Carcasses," *J. Animal Sci.* 38:515–519 (1974).

Suryarachchi et al., "Occurrence and Growht of Yeasts in Yogurts," *App. & Env. Microbiol.* 42:574–579 (1981).

Vedamuthu, "The Use of Candle Oats Jar Incubation for the Enumeration, Characterization and Taxonomic Study of Propionibacteria," *Milchwissenshaft* 22:428–431 (1967).

*Handbook of Food Additives*, CRC Press, 2nd ed., 137–184 (1972).

Lee, et al., *Can. J. Microbiol.* 16:1231–1242 (1970).

Wolford, et al., *Food Ind.* 17:622–625, 726–734 (1945).

Al–Zoreky et al., "Characterization of Propionibacterial Growth Metablites Inhibitory for Gram Negative Bacteria," *Cultured Dairy Products Journal* pp. 4–13 (1993).

Grinstead et al., "Jenseniin'G, a Heat–Stable Bacteriocin Produced by Propionibacterium jensenii P126," *App. & Env. Microbiol.* 57: 701–706 (1991).

Lyon et al., "Partial Purification and Characterization of a Bacteriocin Produced by Propionibacterium thoenii," *App. & Env. Microbiol.* 57: 701–706 (1991).

Lyon et al., "Inhibition of Psychrotrophic Organisms by Propionicin PLG–1, a Bacteriocin Produced by Propionibacterium thoenii," *J. Dairy Sci.* 76: 1506–1513 (1993).

*Primary Examiner*—Toni R. Scheiner
*Assistant Examiner*—Sheela J. Huff
*Attorney, Agent, or Firm*—Klarquist Sparkman Campbell Leigh & Whinston, LLP

[57] ABSTRACT

A peptide, produced by propionibacteria, has a molecular weight of between 300 and 1200 daltons and is inhibitory to gram-negative bacteria. The peptide can be produced by purification of a propionibacteria metabolite mixture, by chemical synthesis, or by a host transformed with a recombinant vector, and is useful in preventing and treating bacterial infections.

10 Claims, No Drawings

PROPIONIBACTERIA PEPTIDE MICROCIN

CROSS REFERENCE TO RELATED APPLICATIONS

This is a continuation-in-part of application Ser. No. 852,292 filed Mar. 16, 1992, now U.S. Pat. No. 5,260,061, which is a continuation-in-part of application Ser. No. 192,231, filed May 9, 1988, now U.S. Pat. No. 5,096,718, which is a continuation-in-part of application Ser. No. 753,563, filed Jul. 10, 1985, now abandoned, which is a continuation-in-part of application Ser. No. 419,559, filed Sep. 17, 1982, now abandoned. Each of the prior applications is incorporated herein by reference.

SUMMARY OF THE INVENTION

The present invention relates to newly discovered substances which are bacteriocins produced by propionibacteria. These bacteriocins have application in development of preservative systems for food, in improving their own production by microorganisms, and in medicine.

The need for improved methods of food and feed preservation is great; activities of bacteria, molds, and yeasts render millions of pounds of food inedible annually and the problem is especially acute in countries with inadequate refrigeration. Many bacteria, molds, and yeasts also cause local and systemic infections in humans and animals which are often so serious as to be life threatening. Many microorganisms which spoil food or cause infections are resistant to the agents currently in use. This is especially true for gram-negative bacterial infections in burn patients, as one example. And, new agents are needed to inhibit or kill *Helicobacter pylori* (a gram-negative organism) which is now thought to be the leading cause of ulcers in people. Thus, there is a need for new antimicrobial agents for use in medicine and in preservation of food and feed.

Microbial metabolites, such as bacteriocins and especially so-called antibiotics, which inhibit the growth of microorganisms are well-known. Indeed, a large segment of the pharmaceutical industry is based on the sale of purified anti-microbials which find uses in medicine and to some extent also in the food industry.

Lactic streptococci (lactococci) are commonly used in dairy fermentations to produce cheeses. An article by Geis et al. (Geis, Singh and Teuber, "Potential of Lactic Streptococci to Produce Bacteriocin," *Applied and Environmental Microbiology*, 205–211 (1983)) showed that about 5% of 280 strains investigated produced bacteriocins. It is significant that none of these bacteriocins acted on gram-negative bacteria.

Bacteriocins are an extremely heterogeneous group of substances. The original definition of bacteriocins referred to proteins of the colicin type produced by *Escherichia coli* (Jacob, F. A., A. Lwoff, A. Siminovitch, and E. Wollman, "Définition de Quelques Termes Relatifs à la Lysogénie," *Ann. Inst. Pasteur Paris.* 84:222–224 (1953). Produced by strains of gram-positive and gram-negative bacteria, they were characterized by lethal biosynthesis, intraspecific activity, and adsorption to specific receptors (Tagg, J. R., and A. R. McGiven, "Assay System for Bacteriocins," *Appl. Environ. Microbiol.* 21:943 (1971)). Tagg et al. defined bacteriocins as active macromolecules possessing a narrow inhibitory spectrum of activity, protein in nature, plasmid encoded and without effect on producer cells. Reports have shown that, unlike most bacteriocins produced by gram-negative bacteria which act on closely related species, bacteriocins from gram-positive bacteria have been shown also to inhibit gram-negative organisms (Wolff, L. F., and J. L. Duncan, "Studies on a Bactericidal Substance Produced by Group A Streptococci," *J. Gen. Microbiol.* 81:413–424 (1974); Silva, M., N. W. Jacobus, C. Deneke and S. L. Gorbach, "Antimicrobial Substance from a Human Lactobacillus Strain," *Antimicrob. Agents Chemother.* 31:1231–1233 (1987); Bhunia, A. K., M. C. Johnson and B. Ray, "Purification, Characterization and Antimicrobial Spectrum of a Bacteriocin Produced by *Pediococcus Acidilactici*," *J. Appl. Bacteriol.* 65:261–268 (1988); Lyon and Glatz 1991; Lewus, C. B., A. Kaiser, and T. Montville, "Inhibition of Food-Borne Bacterial Pathogens by Bacteriocins from Lactic Acid Bacteria Isolated from Meat," *Appl. Environ. Microbiol.* 57:1683 (1991)). On the other hand, Klaenhammer (Klaenhammer, Todd R., "Bacteriocins of Lactic Acid Bacteria," *J. Biochimie.* 70:337–349 (1988)) pointed out that inhibition of gram-negative bacteria has not been clearly demonstrated by purified bacteriocins from gram-positive organisms. In this regard, the presence of a lipoteichoic acid receptor for pediocin AcH in the host cell wall suggested that the bacteriocins from gram-positive bacteria may not be inhibitory to gram-negative organisms since they do not possess cell wall teichoic acid (Bhunia, A. K., M. C. Johnson, B. Ray, and N. Kalchayanand, "Mode of Action of Pediocin AcH from *Pediococcus acidilactici* H on Sensitive Bacterial Strains," *J. Appl. Bacteriol.* 70:25–33 (1991)).

Many strains of gram-positive fermentation starter culture bacteria produce bacteriocins such as Nisin, Diplococcin, Leuconocin Lcm, Mesenteroicin 5, Pediocin AcH, Pediocin PA1, Pediocin A, Lactacin A, Lactacin F, Acidophilucin A, Plantacin B, Plantaricin A, Lacticin, Lactocin 27, Helveticin J, Brevicin 37, Sakacin A, Lactocin S, and Bifidin (Ray, Bibek and Daeschel, Mark, "In Bacteriocins of Starter Culture Bacteria as Food Biopreservatives: An Overview," *Food Biopreservatives of Microbial Origin* CRC Press, Boca Raton, Fla. Ch.8, 177–205 (1992)). These bacteriocins possess narrow or wide spectra of activity. However, it is those with the wider range of activity that are desirable as food biopreservatives. Characteristics that defined a bacteriocin have been expanded to include their chemical nature, stability, mode of action, genetic determination, inhibitory spectrum, sensitivity to various proteases, mode of synthesis, and toxicity level to animals (Ray, Bibek and Daeschel, Mark, "In Bacteriocins of Starter Culture Bacteria as Food Biopreservatives: An Overview," *Food Biopreservatives of Microbial Origin* CRC Press, Boca Raton, Fla. Ch.8, 177–205 (1992)). The molecular weights of bacteriocins vary greatly. They have been classified into small or large molecular-weight groups. In general, low molecular weight bacteriocins are sensitive to trypsin digestion but insensitive to heat inactivation (Bradley, D. E., "Ultrastructure of Bacteriophages and Bacteriocins," *Bacteriol. Rev.* 31:230–314 (1967)). Caseicin 80, a large bacteriocin is produced by *Lactobacillus casei* and has a molecular weight of 40,000 daltons (Rammelsberg and Radler 1990). A well characterized low molecular weight bacteriocin (2500 daltons) is produced by *Lactobacillus acidophilus* (Muriana, P. M. and T. R. Klaenhammer, "Purification and Partial Characterization of Lactacin F, a Bacteriocin Produced by Lactobacillus acidophilus," 11088. *Appl. Environ. Microbiol.* 57:114–121 (1991)).

Another group of amino acid-peptide antimetabolites of low molecular weight (<5000 daltons) produced by enterobacteria has been reported. Microcin C7 is a bacteriostatic antibiotic of about 900 daltons in size. It is resistant to heat treatment (100° C., 30 minutes) but sensitive to trypsin and subtilisin (Baquero, F. and F. Moreno, "The Microcins," *FEMS Microbiol. Lett.* 23:117–124 (1984)). Amino acid analysis of Microcin C7 showed a linear octapeptide of moderate polarity. The structure consists of acetyl-methionine, arginine, threonine, glycine, asparagine, and alanine with an ethanolamine at its carboxyl terminus. Microcin D140 (–500 daltons) is a highly hydrophilic basic peptide with sensitivity to trypsin and subtilisin (Garc ia-Bustos, J. F., N. Pezzi, and C. Asensio, "Microcin 7: Purification and Properties," *Biochem. Biophy. Res. Comm.* 119:779–785 (1984)). The spectrum of activity of these microcins includes inhibition for Escherichia spp., Salmonella spp., Shigella spp., Citrobacter spp., Klebsiella spp., and Enterobacter spp. However, Pseudomonas spp. and Acinetobacter spp. are resistant (Baquero, F. and F. Moreno, "The Microcins," *FEMS Microbiol. Lett.* 23:117–124 (1984)).

Propionibacteria are gram-positive organisms which produce propionic acid. Anderson (U.S. Pat. No. 4,497,833) teaches that propionibacteria metabolites which contain enough propionic acid to inhibit mold can be used to grow yeasts in bread production. Meade and Stringham (U.S. Pat. No. 2,465,905) use a mature culture of mixed metabolites of *Propionibacterium shermanii* as a nutrient broth to grow bacteria (*Lactobacillus bulgaricus*). Meade teaches that propionates do not inhibit bacterial growth. James Sherman (U.S. Pat. No. 1,937,672) also shows the growth of a bacterium (*Lactobacillus casei*) with *Bacterium acidipropionici*, and states that bacteria other than the *Lactobacillus casei* can be used with propionibacteria. Thus, mixed metabolites of propionibacteria are known and are used to support bacterial growth.

Propionibacteria are reported to produce an antiviral component (Ramanathan, Read and Cutting, "Purification of Propionin, An Antiviral Agent from Propionibacteria," *Proc. Soc. Exp. Biol. Med.* 123:271–273 (1966); Ramanathan, Wayne and Cutting, "Antiviral Principles of Propionibacteria," Isolation and Activity of Propionics B and C," *Proc. Soc. Exp. Biol. Med.* 129:73–77 (1968)).

It is now discovered that propionibacteria produce a peptide or protein material of molecular weight of between 800 and 1200 daltons. The material is effective to inhibit gram-negative organisms and can be bactericidal. This material has usefulness in medicine and food preservation.

It is therefore a general object of the present invention to provide a purified peptide material suitable to inhibit or kill gram-negative spoilage or infectious bacteria. There are also a number of specific objects relating to various different aspects of the invention, including the following.

One specific object is to provide such a peptide material that is suitable for use in medicine or for medical treatment.

It is a further object to provide such a peptide material that is suitable for topical or systemic use in animals.

A related object is the treatment of burn patients by topical or systemic use of such a peptide material.

A further object is the use of such a peptide material to treat ulcer patients or to inhibit the gram-negative bacteria *Helicobacter pylori*.

It is a further object provide such a peptide material by chemical synthesis.

It is an object to provide such a peptide material by using the amino acid sequence of the peptide material to construct genetic probes to select DNA for insertion into plasmids which can be genetically introduced into microorganisms, including microorganisms other than the original producer, to produce the microcin peptide.

It is a further object to preserve feed and food using the microorganisms which receive the genetic information and thus produce the microcin peptide.

These and other objects will become increasingly apparent by reference to the following description and examples.

DETAILED DESCRIPTION

For the purpose of this disclosure, "bacteriocin" is used within a broad or general definition to mean a peptide or protein material which is inhibitory or killing to microorganisms other than the producing microorganism. Specifically, a bacteriocin produced by propionibacteria has action against gram-negative bacteria as revealed herein.

It is discovered that the bacteriocin can be purified and is a peptide of molecular weight greater than 300 and less than 1200, which can be referred to by the general term "microcin". Specifically, a new microcin is discovered which has a molecular weight of between 800 and 1200 daltons.

EXAMPLE 1

This example shows that many different propionibacteria can produce metabolites which are inhibitory to a variety of gram-negative microorganisms. Examples which follow show that metabolites other than propionic acid are inhibitors of the gram-negative microorganisms. All gram-negatives tested are food spoilage organisms which were isolated from spoiled cottage cheese.

100 ml bottles of non-fat milk fortified with 0.1% yeast extract were autoclaved and cooled to 30° C. After acidification to pH 5.3 with 10% lactic acid, each was inoculated with 1–2% of a 96-hour old culture of Propionibacterium starter. Each Propionibacterium starter was grown in sodium lactate broth (Tripticase, 10.0 g; yeast extract, 10.0 g; 60 percent sodium lactate solution, 16.7 ml; monopotassium phosphate, 0.25 g; manganous sulfate, 0.005 g or 0.5 ml of a 0.1M solution; and water, 1000 ml; pH 7.0 before autoclaving at 121° C. for 15 minutes) at 30° C. Flasks were placed on a six station magnetic stirrer and slowly agitated during the entire incubation period.

After 96 hours of incubation at 30° C., the pH of all cultures was adjusted to 6.0 with 10% sodium hydroxide, followed by pasteurization. Samples of each were then assayed against six different gram-negative bacteria using a Well Assay Standard Procedure (see Example below).

The following tables represent inhibitory activity (expressed as the diameter of the zone of inhibition as measured in mm) of the metabolites of ten different propionibacteria assayed against six different gram-negative bacteria. Potassium sorbate (10%) and uninoculated skim milk were used as controls.

TABLE I

INHIBITORY ACTIVITY OF PROPIONIBACTERIA METABOLITES AFTER 4 DAYS OF INCUBATION

| Ent. NUMBER | PROPIONIBACTERIA SPECIES DESIGNATION | STRAIN NUMBER | Ps. putida | Ps. fluorescens | Ps. aeruginosa | Ps. maltophilia | cloacae | E.coli |
|---|---|---|---|---|---|---|---|---|
| P1 (ISU) | P.freudenreichii subsp. shermanii | F$_{24}$ | 10 | 13 | 11 | 0 | _10_ | _12.5_ |
| P7 (ISU) | P.freudenreichii subsp. shermanni | 52 | _10_ | 10 | _11_ | 0 | 0 | 0 |
| P12 (ISU) | P.freudenreichii subsp. shermanii | 58 | _10_ | 11 | _11.5_ | 9 | 0 | 0 |
| P15 (ISU) | P.thoenii | TH20 | 13 | 13 | 14 | 18 | _10_ | _14_ |
| P25 (ISU) | P.jensenii | J17 | 0 | 0 | 0 | 0 | 0 | 0 |
| P31c (ATCC) | P.shermanii | | 19 | 25 | 17.5 | 19 | 21 | 24 |
| 4874 (ATCC) | P.thoenii | | 0 | 0 | 0 | 0 | 0 | 0 |
| 4869 (ATCC) | P.jensenii | | 0 | 0 | 0 | 0 | 0 | 0 |
| 6207 (ATCC) | P.freudenreichii | | 0 | 0 | 0 | 0 | 0 | 0 |
| 9616 (ATCC) | P.shermanii | | 13 | 13 | 14 | 0 | 0 | _14_ |
| Control | | | 0 | 0 | 0 | 0 | 0 | 0 |
| Sorbate | | | 12 | 12.5 | 10 | 30 | 18 | |

Note:
Underlined numbers indicate a very hazy zone
ISU is the number for cultures obtained from Iowa State University, Department of Food Technology, Propionibacteria Culture Collection.
ATCC is the American Type Culture Collection number. The well size is 6 mm in diameter and the total diameter of inhibition including the well is measured, except when there is no inhibition observed. Thus, a number of 10 means the well plus the inhibition zone is 10 mm while a 0 means no inhibition around the 6 mm well.
For the gram-negative food spoilage bacteria, Ps. represents Pseudomonas.

TABLE II

INHIBITORY ACTIVITY OF PROPIONIBACTERIA METABOLITES AFTER 7 DAYS OF INCUBATION

| Ent. NUMBER | PROPIONIBACTERIA SPECIES DESIGNATION | STRAIN NUMBER | Ps. putida | Ps. fluorescens | Ps. aeruginosa | Ps. maltophilia | cloacae | E.coli |
|---|---|---|---|---|---|---|---|---|
| P1 (ISU) | P.freudenreichii subsp. shermanii | F$_{24}$ | 13 | 12 | 12 | 27 | 0 | 0 |
| P7 (ISU) | P.freudenreichii subsp. shermanni | 52 | 13 | 14 | 14 | 16 | 0 | 13 |
| P12 (ISU) | P.freudenteichii subsp. shermanii | 58 | 14 | 14 | 14 | 0 | 0 | 15 |
| P15 (ISU) | P.thoenii | TH20 | 13 | _15_ | 13 | 0 | 0 | 0 |

TABLE II-continued

INHIBITORY ACTIVITY OF PROPIONIBACTERIA METABOLITES AFTER 7 DAYS OF INCUBATION

| | PROPIONIBACTERIA | | | Gram-Negative Food Spoilage Bacteria | | | | | |
|---|---|---|---|---|---|---|---|---|---|
| Ent. NUMBER | SPECIES DESIGNATION | STRAIN NUMBER | Ent. cloacae | E.coli | Ps. putida | Ps. fluorescens | Ps. aeruginosa | Ps. maltophilia |
| P$_{25}$ (ISU) | P.jensenii | J17 | 0 | 0 | 0 | 0 | 0 | 0 |
| P$_{31c}$ (ATCC) | P.shermanii | | 0 | 0 | 13.5 | 12 | 14 | 0 |
| 4874 (ATCC) | P.thoenii | | 0 | 0 | 0 | 0 | 0 | 0 |
| 4869 (ATCC) | P.jensenii | | 0 | 0 | 0 | 0 | 0 | 0 |
| 6207 (ATCC) | P.freudenreichii | | 0 | 0 | 0 | 0 | 0 | 0 |
| 9616 (ATCC) | P.shermanii | | 0 | <u>14</u> | 13 | 11 | 13.5 | 0 |
| Control | | | 0 | 0 | 0 | 0 | 0 | 0 |
| Sorbate | | | 18 | 25 | 12 | 14 | 11 | 35 |

Note:
Underlined numbers indicate a very hazy zone
ISU is the number for cultures obtained from Iowa State University, Department of Food Technology, Propionibacteria Culture Collection.
ATCC is the American Type Culture Collection number. The well size is 6 mm in diameter and the total diameter of inhibition including the well is measured, except when there is no inhibition observed. Thus, a number of 10 means the well plus the inhibition zone is 10 mm while a 0 means no inhibition around the 6 mm well.
For the gram-negative food spoilage bacteria, Ps. represents Pseudomonas.

Data in the tables show that all of the gram-negative microorganisms tested were inhibited by at least one species of propionibacteria. The potassium sorbate control required a 10% solution to show effects comparable to the metabolites of propionibacteria. This is a dramatic finding as sorbates are commonly used as food preservatives but are only used in concentrations of about 0.1% or 100 times less than required in these controls.

Data also show that the activity is related to incubation time in some cases (compare 4 days of incubation data to 7 days of incubation data). Of course, it is relatively easy to optimize incubation time. The inhibition is due to some metabolite or metabolites other than propionic acid (see further Examples). Further, data in the tables show that propionibacteria metabolite inhibition of gram-negative microorganisms is variable within propionibacteria species and subspecies or strains. This has not previously been known because it has not even been previously known that such inhibition of gram-negative microorganisms occurs. Now that such an effect is known, it is relatively easy to "screen" species of propionibacteria to identify those which produce a metabolite or metabolites as disclosed herein.

EXAMPLE 2

*Propionibacterium shermanii* (ATCC Strain 9616) was grown in a sodium lactate broth for 96 hours. Five hundred gallons of skim milk were then pasteurized at 190° F. for 45 minutes, and subsequently cooled to 86° F. The cooled milk was acidified using 85 percent reagent grade lactic acid to a pH of 5.3 and then inoculated with 0.5% of the *Propionibacterium shermanii* culture. The inoculated milk was slowly agitated during incubation for 48 hours, and thereafter neutralized with sodium hydroxide to pH 7.0. The neutralized liquid was pasteurized at 145° F. for 20 minutes, cooled to ambient temperature (about 75° F.), pumped through sterile lines into six-gallon sterile plastic bags and then frozen.

When thawed, the liquid medium was very active in inhibiting the growth of slime producing, psychotropic, gram-negative spoilage organisms isolated from cottage cheese.

EXAMPLE 3

Partial Characterization of Metabolites of Propionibacteria Affecting Inhibitor Growth The molecular weight of a microbial inhibitor produced by propionibacteria was estimated using Bio-Gel P4 (Bio-Rad) gel filtration which separates molecules based on their molecular weights compared to known molecular weight standards.

A sample of propionibacteria metabolites produced in dextrose broth by growing propionibacteria 9616 for four days was mixed with standards of known molecular weight and applied to the column. Each fraction collected was assayed for inhibition of gram-negative psychrotropic bacterial growth using a standard well assay (procedure shown below).

Of over 100 fractions collected, anti-microbial activity was only detected in samples 21 to 25. The peak fraction of activity corresponds to a molecular weight of approximately 1,000. The exact molecular weight is not determined from this size exclusion chromatography and the molecular size may range from about 600 to 1200. No activity whatsoever was detected in fractions corresponding to the molecular weight of propionic acid (MW 74.1), i.e. fractions 90 to 98 (not shown). Virtually 100% of the activity applied to the column was recovered in the active fractions. Clearly the most active propionibacterial metabolite responsible for inhibiting gram-negative growth is not propionic acid. These data show that at least one metabolite other than propionic acid has an inhibitory effect on gram-negative bacteria. The column data are not exclusive in that the highest molecular weight control was Vitamin B-12, molecular weight 1,350. Other metabolites may certainly exist with molecular weights other than about 1,000 which are not propionic acid and which do inhibit microorganisms. In fact, some preliminary research using electrophoresis gels suggest a substance with molecular weight about 13,000 is produced by propionibacteria which is inhibitory to gram-negative microorganisms. These types of experiments do not allow determination of exact quantities of active metabolites. Thus, it is not currently possible to refer to concentrations or amounts of the purified metabolites which would be effective. However, the scope of this invention includes such purified metabolites. Thus, we disclose that microorganism inhibitors of molecular weight greater than a few hundred (and certainly greater than propionic acid) are produced by propionibacteria, which has not previously been known. These new metabolites are referred to herein as metabolites of molecular weight greater than 300 which have antimicrobial activity. These substances will have a variety of uses as inhibitors of gram-negative bacteria. For example, Pseudomonas is greatly inhibited by the newly discovered active metabolites and Pseudomonas present a dire medical problem for treatment, especially in burn patients and some systemic infections. This new compound can also be used to inhibit *Helicobacter pylori*, also a gram-negative bacterium, which is now thought to be the primary cause of ulcers in humans. The newly discovered nonpropionic acid metabolite(s) of propionibacteria can be isolated, purified and utilized, in purified or semi-purified form, to inhibit such gram-negative bacteria.

Additional evidence that there is a propionibacterial metabolite responsible for yeast inhibition which is not propionic acid is shown by the data below (Table III) demonstrating that no correlation exists between propionic acid concentrations and yeast inhibition. In this experiment, two lots of inhibitor prepared as in Example 2 were found to have significantly different propionic acid concentrations. However each were shown to be equally effective in inhibiting yeast growth (assay procedure below).

As a control, skim milk with added propionic acid was assayed for its inhibitory nature against yeast in an identical fashion. No inhibition was detected at any level of propionic acid tested, confirming that propionic acid is not the yeast inhibitor in propionibacteria metabolites. These data show that certain propionibacteria produce at least one metabolite other than propionic acid, which has a molecular weight greater than 300, and has an inhibitory effect on a food spoilage yeast, and that a material containing the metabolite can be provided in a food product normally devoid of propionibacteria in an amount sufficient for the metabolite to inhibit yeast.

TABLE III

PERCENT INHIBITION OF YEAST GROWN IN THE PRESENCE OF INHIBITOR

| Mixture | % Inhibitor* | | % Inhibition | | % Propionic Acid in Final |
|---|---|---|---|---|---|
| | Control Colonies: | 800 | 78 | 8 | |
| LOT NO. 023 | 1 | 25 | 50 | 100 | .0023 |
| | 5 | 75 | 100 | 100 | .0165 |
| | 10 | 100 | 100 | 100 | .0230 |
| LOT NO. 343 | 1 | 25 | 50 | 100 | .0002 |
| | 5 | 50 | 75 | 100 | .0010 |
| | 10 | 100 | 100 | 100 | .0020 |
| LOT NO. 023 | 2,270 ppm propionic acid (0.227%) | | | | |
| LOT NO. 343 | 243 ppm propionic acid (0.024%) | | | | |

PERCENT INHIBITION OF YEAST GROWN IN THE PRESENCE OF SKIM MILK PLUS PROPIONIC ACID

| Mixture | % Additive* | | % Inhibition | | % Propionic Acid in Final |
|---|---|---|---|---|---|
| | Control Colonies: | 2000 | 187 | 25 | |
| SKIM PLUS | 1 | 0 | 0 | 0 | .0023 |
| 243 ppm | 5 | 0 | 0 | 0 | .0165 |
| Propionic Acid | 10 | 0 | 0 | 0 | .0230 |
| SKIM PLUS | 1 | 0 | 0 | 0 | .0002 |
| 2270 ppm | 5 | 0 | 0 | 0 | .0010 |
| Propionic Acid | 10 | 0 | 0 | 0 | .0020 |

*Percent of propionibacterial metabolites added to potato dextrose agar (PDA) containing yeast (See Yeast Assay which follows).
**Percent of additive (which was skim milk containing added propionic acid) added to potato dextrose agar (PDA) containing yeast.

The present invention differs further from any previous teachings as it is now revealed that there are propionibacteria metabolites of molecular weight greater than 300 and of about 700 to 1200 and also perhaps of about 13,000 which inhibit yeasts, mold and bacteria.

Efforts were taken to determine whether the metabolite responsible for inhibiting the growth of gram-negative bacteria was amino acid or polypeptide or protein in nature. Samples of Inhibitor were treated with a variety of proteolytic enzymes (see Table IV). As is shown, the action of three of the four enzyme treatments eliminated the antimicrobial activity, suggesting an amino acid or polypeptide or protein nature. It is anticipated that isolation and purification or semi-purification of the active metabolite will find broad usage as an inhibitor of undesirable gram-negative microorganisms.

TABLE IV

EFFECT OF PROTEOLYTIC ENZYMES ON THE INHIBITORY ACTIVITY OF INHIBITOR

| ENZYMES | INHIBITORY ACTIVITY AFTER TREATMENT |
|---|---|
| Protease (papaya) | – |
| - Chymotrypsin | – |
| Pepsin | – |
| Trypsin | + |

1% Inhibitor (prepared as in Example 2) was treated with each enzyme at a concentration of 0.1% w/v and at the optimal pH for each. After standard incubation, the enzymes were inactivated by heat, the pH adjusted and the samples assayed against *P. putida*. Enzymatically untreated Inhibitor was used as a control.

Well Assay Standard Procedure

Medium Used—crystal violet tetrazolium (CVT) agar that has been adjusted to pH 5.3, 17 ml per plate. (See procedure below for CVT composition). Plates should be made at least 48 hours before use.

Lawn—Use an appropriate gram-negative organism e.g. *P. putida*. Grow culture overnight (24 hrs) in lactose broth at 30° C. Dilute with sterile peptone water about 1:10–1:100 until a reading of 90% transmittance is obtained at 595 nm.

Add 2 drops from a 1.0 ml pipet of above solution and spread on one of the plates. When lawn has "dried", cut and remove wells. Add 2 drops test liquid per well and incubate overnight.

CVT agar (per liter of water add 5 g tryptone, 2.5 g yeast extract, 1.0 g glucose, 1.0 ml of a 0.1% solution of crystal violet in ethanol solution, and 15.0 g agar, adjust pH to 7.1) is mixed, placed in a steamer until melted, pour in 100 ml volumes in dilution bottles, and autoclave for 15 minutes at 121° C. After autoclaving, the bottles of CVT agar were placed in a 46° water bath. After the agar was cooled, each bottle had added 0.4 ml of a 10% sterile solution of tartaric acid in water and 1.0 ml of a filter sterilized 1.0% solution of 2, 3, 5-triphenyl-2H-tetrazolium chloride (TTC) in water. The pH should be 5.3.

Yeast Assay and Inhibitor

An assay against yeast was conducted using potato dextrose agar (PDA), acidified to pH 4.0 and supplemented with INT to distinguish colonies from debris. INT is p-Iodonitrotetrazoliun Violet and is obtained from Sigma Chemical (Cat. #I-8377). It is prepared as a 0.29% solution in water and filter sterilized. Do not autoclave. INT is used at a level of 0.5 ml per 100 ml of melted and cooled agar. Colonies growing in the presence of INT will take on a red color.

Colonies on the plate will eventually "catch up" to the controls. As a result, the colonies are incubated at room temperature for two days and then read. There should be a significant size difference (indicating fewer numbers of cells) between Inhibitor and control plates. The "catch up" effect and the size difference in colonies both indicate a micro-static effect rather than a micro-cidal effect.

EXAMPLE 4

Skim milk was fermented with *Propionibacterium shermanii* (ATCC Strain 9616) with some agitation to prevent development of large cheese curds. The resulting composition, including all the bacterial metabolites, was freeze-dried. Fifteen grams of freeze-dried composition were added to 85 ml of water and acidified with hydrochloric acid to a pH of 4.6. This reconstituted mixture was then centrifuged at 10,000 rpm for 20 min at 4° C., and the supernatant sterilized by passing it through a 0.22 filter. The clarified supernatant fraction was then applied to a Sephadex G-25 column that was previously equilibrated with 0.2M sodium chloride to control viscosity and contamination. The flow rate of the column was 7.5 ml per hour.

Each fraction of the column was assayed for inhibitory activity by way of a plate assay. Crystal violet tetrazolium agar, acidified to pH 5.3, is selective for gram-negative organisms and was used for the assay. One ml samples of serial dilutions of overnight cultures of psychotropic gram-negative spoilage organisms isolated from cottage cheese were mixed with CVT agar that contained various levels of the fraction to be tested.

Inhibitory properties of 70 fractions collected from the G-25 column varied from fraction to fraction, but it is clear that some fractions with molecular weights much different than propionic acid had substantial inhibiting properties. Ten separate fractions showed major inhibitory properties (100 percent inhibition of $10^4$ dilution of organisms) while several other fractions had lesser activity (100 percent inhibition of $10^6$ dilution of organisms). These partially purified fractions were so potent as to be bactericidal in some cases. They represent molecular weights of greater than 300 and, as seen in the example above, molecular weights of between 700 and 1200. This experiment shows that the unique materials described herein can be separated by densities and by molecular weight and can be concentrated by freeze drying.

EXAMPLE 5

Further effort was directed towards determining the molecular weight of the active peptide or protein material (bacteriocin or microcin) identified in the above examples. A 20×2.5 cm sephadex G-10 column (Sigma) was used to separate the active component(s) of a material grown as in Example 2. The flow rate was 2 ml/min. sodium chloride (0.2M) was used to equilibrate the column as the eluent at room temperature. The molecular weight standards used were Bacitracin (1422), sleep-inducing peptide (848) and tyrosine (217.7). All were Sigma products. Each solution was prepared by dissolving 2.5 mg of each compound in one ml deionized water. Then two ml of each solution was loaded separately into the column and eluted with sodium chloride and fractions were collected manually. Each fraction was five ml. The absorbance of each was determined at 280 nm using a Beckman DU-40 spectrophotometer. A Standard curve was obtained by plotting the log of molecular weight against fraction number. Samples were used in a disc assay against *P. putida* to test for inhibition of the bacterium. Fractions (both active and inactive) were quantified for the level of protein using a Beckman DU-40 spectrophotometer (nucleic acid Soft-Pac module, part #533126, Warburg and Christain program 10), which gives the concentration of protein as mcg/ml.

The fractions which inhibit gram-negative bacteria eluted from the column between the sleep-inducing peptide and the tyrosine and the molecular weight was estimated to be about 750 daltons from the log molecular weight vs. fraction number standard curve which was nearly linear. The active components eluted from the Sephadex column gave a positive Biuret test indicating the presence of protein. Protein concentrations were about 200 µg/ml in the main active fractions. Active fractions were heat stable and had a maximum absorbance in the UV range indicating the presence of peptide bonds. The mixture containing the active microcin peptide was bacteriostatic in concentrations of 1% but was bacteriocidal (killed the test organism) upon addition of 5%. This was determined by adding active culture of the gram-negative *P. putida* in tryptone, yeast extract, and glucose broth at 10-4 to 10-7 CFU/ml, adding the microcin containing mixture, incubating at 30 degrees C for 44 hours, and then recovering cells which survived, if any did survive.

EXAMPLE 6

This example shows extensive efforts to identify the active bacteriocin and confirms that a new and previously unknown peptide microcin has been identified. Bacteriocin producer *Propionibacterium freudenreichii* ssp. shermanii strain 9616 was used in the fermentation of grade A skim milk, at 30° C., neutralized to pH 6.30 and then pasteurized. The test organism which was inhibited was the gram-negative *Pseudomonas putida* ATCC 12633 which was grown in lactose broth for 18 hours at 30° C. ($OD_{700}$ 0.1). Plate count agar (Difco Laboratories, Detroit, Mich.) was adjusted with a 10% tartaric acid solution to pH 5.30. 100 ml of dissolved Plate Count Agar was dispensed into each dilution bottle. All media were autoclaved at 121° C. for 15 minutes.

A modified agar-well diffusion method (Tagg, J. R., and A. R. McGiven, "Assay System for Bacteriocins," *Appl. Environ. Microbiol.* 21:943 (1971)) was used to examine the activity of the bacteriocin extracts from the propionibacteria fermentation. Overnight culture of *Pseudomonas putida* (ATCC 12633) was used as indicator strain for the routine bacteriocin assays. Plate count agar was tempered to 45° C. before being inoculated with 0.5 ml of overnight culture of indicator strain. This was followed by the addition of 2 ml of 2, 3, 5-triphenyltetrazolium chloride (1% stock) solution. A 100 ml of this mixture was poured onto each sterile petri-plate (VWR Scientific Company, Inc., West Chester, Pa.) and allowed to solidify at room temperature for 1 hour. The wells (0.75 cm diameter×1.0 cm depth) in the plate count agar were aseptically created by a hole-borer. A volume of 100 ul sample was placed in each well. Bacteriocin titers were determined by a one to one serological dilution, i.e., one volume of bacteriocin diluted in one volume of diluent (1:2). Diluent of 0.1% peptone water was used in the critical dilution assay. Activity was defined as the reciprocal of the last serial dilution demonstrating inhibitory activity and presented as activity units (AU) per milliliter. All culture plates were incubated at 30° C. for 18 hours.

Absorbance at 217 nm was used to monitor the presence of protein in fractions from gel filtration chromatography. Active fractions from ultra-filtration, gel filtration, anion exchange, and HPLC were assayed for their protein contents by the method of Lowry et al. (Lowry, O. H., N. J. Rosebrough, A. L. Farr, and R. J. Randall, "Protein Measurement with the Folin Phenol Reagent," *J. Biol. Chem.* 193:265–275 (1951)) using bovine serum albumin as the standard (700 nm). The procedures for this assay are described in the Lowry Total Protein Assay Kit, No. 5656 (Sigma Chemical Co., St. Louis, Mo.). All bacteriocin purification procedures were performed at 4° C. unless otherwise stated.

pH Adjustment, Centrifugation, and Ultra Filtration

The propionibacteria fermentation product (50 ml) was adjusted to pH 4 with anhydrous tartaric acid (Sigma Chemical Co., St. Louis, Mo.) and centrifuged at 10,000×g for 1 hour. The supernatant was decanted and back-neutralized to pH 5.3 with 10% tartaric acid solution. The supernatant was concentrated to a volume of 24 ml with a concentrator RC-1009 (Jouan, Inc. Winchester, Va.). The conditions for concentrating the supernatant were set at 150 millitorr vacuum and a temperature of −45° C. for 1 hour. The supernatant (pH 5.30) was assayed for activity and total protein concentration. A total volume of 24 ml of the concentrated supernatant was ultra-filtered using an Amicon filtration cell unit #8050 (Amicon Division, W. R. Grace & Co. Beverly, Mass.). An initial molecular weight cut-off membrane was used (YM 10>10000 MW) at a pressure of 30 psi. A total of 9.2 ml 10,000 MW ultra-filtrate (10,000-F) was collected. The retentate (10,000-R) was washed with 0.01M sodium acetate buffer (pH 5.3) and 9.2 ml ultra-filtrate (10,000-F) was placed onto another membrane of 5000 daltons (YM 5>5000 MW) to be filtered at a pressure of 40 psi. All retentates (5000-R & 1000-R) collected were washed with 0.01M sodium acetate buffer (pH 5.3). A volume of 6.2 ml of 5000 MW ultra-filtrate (5000-F) was filtered through a 1000 daltons cut-off membrane (YM 2>1000 MW) at 45 psi. This 1000 ultra-filtrate (5.0 ml) was filtered through a 500 daltons cut-off membrane (YC05>500 MW). A volume of 2.0 ml of 500 MW ultra-filtrate was collected. All collected samples were assayed for antimicrobial activity and total protein concentration.

Chromatographic Separations

An Amberlite-OH anion exchanger column (7×250 mm) was equilibrated with 1.0M $NaCO_3$. After equilibration with the $NaCO_3$ solution, the column was washed and re-equilibrated with 0.01M sodium acetate buffer (pH 5.3) before loading of the 1000 MW ultra-filtrate collected as described above. Eluates from anion-exchanger were collected and assayed for activity and protein concentration. The active fractions from the anion exchange column were put onto a Sephedex G-10 column (10×400 mm) after equilibration with 0.01M sodium acetate buffer, pH 5.30. The eluted active fractions were combined and concentrated by another Sephedex G-10 chromatography step. A single fraction was assayed for activity and protein concentration. L-Tyrosine (217.7 MW), Leu-Pro-Pro-Ser-Arg peptide (568.7 MW), and His-Pro-Phe-His-Leu-Leu-Val-Tyr peptide (1025.2 MW) were used (Sigma Chemical Co., St. Louis, Mo.) to establish a molecular weight standard curve.

The concentrated active fraction (250 ul) from the above column chromatography steps was injected into a reversed-phase C-18 column (4×250 mm, Bio-Sil ODS-5S) equilibrated with 0.1% trifluoroacetic acid (TFA), on a high-pressure liquid chromatograph (HPLC). The collection of HPLC fractions was done at room temperature with a linear gradient from 0 to 100% acetonitrile in 0.1% TFA with a flow-rate of 2.0 ml/min. All eluates were evaporated to dryness under vacuum (150 millitorr) at −45° C. for 1 hour and then rehydrated with cold 0.01M sodium acetate buffer (pH 5.30) to a final volume of 500 ul. The eluates from reversed-phase high performance liquid chromatography were assayed for activity and total protein concentration. An active single-peak fraction in sodium acetate buffer (pH 5.30) from the reversed-phase high performance liquid chromatography was sent to Central Services Laboratory, OSU (Corvallis, Oreg.) and AAA Laboratory (Mercer Island, Wash.) for amino acid hydrolysis and sequencing. Amino acid sequence was estimated by Edman degradation and mass spectroscopy.

The purification process resulted in isolation of a new peptide microcin of estimated molecular weight between about 850 and 950 daltons from the propionibacteria metabolites. The 500 MW ultra-filtrate (320 AU/ml: AU=activity units as defined earlier) and retentate (160 AU/ml) were less active when compared to the 1000 MW (640 AU/ml) and 5000 MW ultra-filtrates (640 AU/ml). All retentates except 500 MW's were less active when compared to the ultra-filtrates. The reduction in activity also corresponded to a lesser protein concentration in the retentates. Therefore, the 1000 MW ultra-filtrate was extracted for further purification by anion-exchange chromatography, gel filtration, and reverse-phase high performance liquid chromatography. The specific activities of fractions from the anion-exchanger (17.39 AU/mg) and gel filtration increased greatly (108.7 AU/mg). Reversed-phase high performance liquid chromatography, the final step of purification, produced a single peak of bacteriocin activity which was recovered in about 4.4–6.0% acetonitrile as the mobile phase. The overall purification process resulted in a very high specific activity of 434 AU for the bacteriocin purified in the HPLC step, a 25 fold increase in antimicrobial specific activity.

The molecular weight of purified bacteriocin was estimated to be 859 daltons by gel filtration. The eluting profile from gel filtration showed two active peaks between absorbance 0.80 and 1.30, respectively.

The m/z data from mass spectroscopy showed two peaks that are in a series, 295 and 441.7 which suggest charges of 3 ($MH^{+3}$) and 2 ($MH^{+2}$), respectively. The molecular weight was estimated to be 881.7 from mass spectroscopy.

Initial amino acid hydrolysis of the single-peak fraction from HPLC (Central Services Laboratory, Oregon State University, Corvallis, Oreg.) revealed the possible presence of methionine, valine, glutamate, glycine, serine, and arginine in a decreasing order of concentration. Analysis from another laboratory (AAA Laboratory, Mercer Island, Wash.) suggested that the peptide may consist of methionine, valine, glutamic acid, and possibly glycine. The molecular weight was estimated to be about 926 daltons. It can be seen that the different methods of molecular weight determination give variable results due to the uncertainty involved. However, it can be concluded from the collective data available that the molecular weight is greater than 300 daltons and less than 1200 daltons, and it is very probable that the molecular weight is between 800 and 1200 daltons.

The proteineous nature of the active and acid-free HPLC purified fraction confirms that an antimicrobial agent present in propionibacteria metabolites was a low molecular weight bacteriocin. The presence of peptide bonds and proteineous nature of this inhibitory substance was confirmed by a positive Biruet test with maximum absorbance at 210 nm. In addition, the antimicrobial agent was sensitive to a-chymotrypsin, pepsin, and papain but not trypsin or catalase. The trypsin-resistant characteristic was similar to Linecin A, a bacteriocin produced by *Brevibacterium linens* (ATCC 9175). The low content of basic amino acids probably explains why Linecin A is resistant to trypsin.

The molecular weight of the bacteriocin identified above is smaller than most bacteriocins and is in a special subcategory called microcins. Microcins are particularly difficult to find and identify and propionibacteria have not previously been known to produce microcins. This finding is especially useful as the small molecular weight and peptide structure are generally far more amenable to use in medicine than large molecular weight bacteriocins. Further, microcins are much easier to use to construct genetic probes than the much larger bacteriocins. Initial data presented herein estimated the molecular weight of the partially purified antimicrobial substance at greater than 300 and at about 1000 daltons. Gel filtration estimated the size of this antimicrobial substance to be within the vicinity of 860 daltons. Initial amino acid sequencing of the bacteriocin (Central Services Laboratory, OSU) yielded a methionine residue at the N-terminus. Other than valine from the second cycle of degradation, an amino acid was not detectable upon direct N-terminal sequencing, indicating the possibility of the presence of unusual amino acids or a cyclic oligopeptide (Lowry, O. H., N. J. Rosebrough, A. L. Farr, and R. J. Randall, "Protein Measurement with the Folin Phenol Reagent," *J. Biol. Chem.* 193:265–275 (1951)). The release of a terminal methionine moiety has been seen during the Edman degradation of another microcin (Aguilar, et al., "Microcin 15m from *Escherichia coli*: Mechanism of Antibiotic Action," *Antimicrob. Agents and Chemother* 21:381–386 (1982)).

The antimicrobial activity of the purified bacteriocin reported herein is similar to Microcin A15 (~500 daltons). The release of a methionine moiety under acidic conditions was also observed in Microcin A15 (Baquero, F. and F. Moreno, "The Microcins," *FEMS Microbiol. Lett.* 23:117–124 (1984)). The antimicrobial mechanism of Microcin A15 was related to L-methionine in which homoserine-O-transsuccinylase was inhibited. The inhibition of homoserine-O-transsuccinylase blocks protein synthesis in the methionine biosynthesis pathway (Aguilar, et al., "Microcin 15m from *Escherichia coli*: Mechanism of Antibiotic Action," *Antimicrob. Agents and Chemother* 21:381–386 (1982); Brush, A., and H. Paulus, "The Enzymic Formation of O-acetyl-Homoserine in *Bacillus subtilis* and its Regulation by Methionine and S-adenosylmethionine," *Biochem. Biophys. Res. Comm.* 45:735–741 (1971); Lee, L. W., J. M. Ravel, and W. Shine, "Multimetabolite Control of a Biosynthetic Pathway by Sequential Metabolites," *J. Biol. Chem.* 241:5479–5480 (1966)).

Since there were blank cycles with the Edman degradation of the purified microcin, the possibility of unusual amino acids should not be ruled out. Nisin (Gross, E., and H. Kiltz, "The Number and Nature of a, b-unsaturated Amino Acids in Subtilin," *Biochem. Biophys. Res. Commun.* 50:559–565 (1973)), subtilin (Gross, E., and H. Kiltz, "The Number and Nature of a, b-unsaturated Amino Acids in Subtilin," *Biochem. Biophys. Res. Commun.* 50:559–565 (1973) epidermin (Allgaier, H., G. Jung, R. G. Werner, U. Schneider, and H. Zähner, "Elucidation of the Structure of Epidermin, a Ribosomally Synthesized Tetracycle Heterodetic Polypeptide Antibiotic," *Angew. Chem.* 24:1051–1053 (1985)). (Kellner, R., and G. Jung, "Sequencing of Peptide Antibiotics Containing Unusual Amino Acids," *Biosyst. Eur. News.* 7:2–3 (1989)), and gallidermin (Kellner, R., G. Jung, T. Hörner; H. Zähner, N. Schnell, K. -D. Entian, and F. Götz, "Gallidermin: a New Lanthionine-Containing Polypeptide Antibiotic," *Eur. J. Biochem.* 177:53–59 (1988) have been shown to contain unusual amino acids such as lanthionine or methyllanthionines (Stoffels, G., J. Nissen-Meyer, A. Gudmundsdottir, K. Sletten, H. Holo, and L. F. Nes, "Purification and Characterization of a New Bacteriocin Isolated from a Carnobacterium sp.," *Appl. Environ. Microbiol.* 58:1417–1422 (1992)). Some bacteriocins are known to contain modified amino-acids such as S-(2-aminovinyl)-D-cysteine, lysino- alanine, dehydroalanine, and dehydrobutyrine, the latter two being the precursors of lanthionine and 3-methyllanthionine (Kellner, R., and G. Jung, "Sequencing of Peptide Antibiotics Containing Unusual Amino Acids," *Biosyst. Eur. News.* 7:2–3 (1989)). Incorporation of a lanthionine residue introduces a monosulfur bridge which results in unique peptide ring structures (Kellner, R., G. Jung, T. Hörner, H. Zähner, N. Schnell, K. D. Entian, and F. Götz, "Gallidermin: a New Lanthionine-Containing Polypeptide Antibiotic," *Eur. J. Biochem.* 177:53–59 (1988); Kellner, R., and G. Jung, "Sequencing of Peptide Antibiotics Containing Unusual Amino Acids," *Biosyst. Eur. News.* 7:2–3 (1989).

It is clear that the isolation, structure identification and determination of the mechanism of action for the bacteriocin disclosed herein are very complex and the exact nature is not yet fully known. It is also clear that a new microcin has been identified and partially characterized and the microcin has great potential for application in medical treatment and in preservation in feeds and food. In medicine, the microcin can be used topically or systemically to treat infections caused by susceptible microorganisms which has been shown to include gram-negative bacteria and yeast. Topical application could include application to the stomach membrane to treat for *Helicobacter pylori*. Burn patients with gram-negative infections are prime candidates for the newly discovered microcin. Listeria and some other gram-positive bacteria have been shown to be inhibited in their action by the metabolites of propionibacteria. The purified or partially purified microcin is much more potent than in the nonpurified form and is expected to have much wider action than the original crude mixture of propionibacteria metabolites. Thus, the microcin will find use in medicine and preservation of food and feeds in inhibiting or killing some gram-positive bacteria also.

Peptides are produced in bacterial cells as a result of amino acid sequence codes in genetic material. Once a specific microcin peptide sequence is known, then the information can be used to create genetic probes to locate a DNA sequence that codes for production of the microcin. The sequence can be inserted into plasmids which in turn can be inserted into the same type of bacteria as originally produced the microcin or into other microorganisms such as any of the group of organisms known as lactic acid bacteria, or E. coli or yeast, or others.

For example, the N-terminal amino acid sequence of the purified microcin can be determined on an Applied Biosystems Automated Protein Sequenator (Applied Biosystems, Foster City, Calif.). Based on these N-terminal amino acid sequences, degenerate oligonucleotide probes can be synthesized on an Applied Biosystems DNA synthesizer and employed to clone the genes encoding the microcin. It will be possible to make two degenerate oligonucleotide primers corresponding respectively to the two terminal amino acid residues of the microcin. The primers will be made in opposing orientations so as to amplify the internal region in a polymerase chain reaction (PCR). The PCR reaction will be performed using conventional techniques (Mullis and Faloona, *Methods Enzymol.* 155:335–350 (1987); Innis, et al., "PCR Protocols, a Guide to Methods and Applications," *Academic Press Inc.*, San Diego, Calif. (1990); and the thermostable DNA polymerase from *Thermus aquaticus* DNA Taq polymerase (Saiki, et al., *Science* 239:487–491 (1988)). PCR can be performed in a Coy temperature cycler (Coy Laboratory Products, Inc., Ann Arbor, Mich.) with a temperature profile of 94°–55°–72° C. cycling for 30 sec, 1 min., and 1 min., respectively, for 35 cycles. A fragment can be amplified by PCR, labeled with [α-$^{32}$P] dCTP by random priming (Sambrook, et al., *Molecular Cloning, 2nd ed.*, (1989), Cold Spring Harbor Laboratory, Cold Spring Harbor, N.Y., and used as a probe in genomic DNA and colony hybridizations. Southern hybridization (Southern, 1975) can be used to reveal a BamHI fragment of the propionibacteria genomic DNA hybridized with the probe.

A genomic library can subsequently be constructed as described by Xun and Orser, Xun and Orser, *J. Bacteriol.* 173:2920–2926 (1991a). Total DNA will then be extracted by the method of Birnboim and Doly, Birnboim and Doly, *Nucleic Acids Res.* 7:1513–1515 (1979) and purified by a procedure such as cesium chloride-ethidium bromide density gradient centrifugation (Sambrook, et al., *Molecular Cloning, 2nd Ed.*, (1989) Cold Spring Harbor Laboratory, Cold Spring Harbor, N.Y.). DNA extracted in this manner will be partially digested with BamHI and size fractionated to select for target fragments (Sambrook, et al., *Molecular Cloning, 2nd Ed.*, (1989) Cold Spring Harbor Laboratory, Cold Spring Harbor, N.Y.). A plasmid vector will then be ligated to the BamHI-digested DNA fragments. Ligated molecules will be transduced into *E. coli* HB101 as described by Maniatis, et al. (Maniatis, et al., "Molecular Cloning: A Laboratory Manual," (1982), Cold Spring Laboratory, Cold Spring Harbor, N.Y.). Transductants will be selected on agar plates. Hybridization will be performed using the fragment labeled with [α-$^{32}$P] dCTP by random priming as described by Sambrook et al. (Sambrook, et al., *Molecular Cloning, 2nd Ed.*, (1989) Cold Spring Harbor Laboratory, Cold Spring Harbor, N.Y.). Positive colonies will contain the gene encoding the microcin.

When the microcin is produced in culture, it is preferably isolated and purified. Purification can be accomplished by ultrafiltration and HPLC.

Determining the exact structure of the microcin has not yet been completed as the extensive isolation and purification has been done on a small scale beginning with only 50 ml of the cultured material which has provided only a very small amount of the microcin (one ml of diluted solution) from the standard HPLC column work. However, now that the presence of the new peptide molecule is taught and extensively verified, preparative scale HPLC columns and larger quantities can be used to isolate the peptide in sufficient quantity to conduct repeated HPLC purification steps, and repeated mass spectra data and Edman degradation and NMR can be used to determine the exact structure of the microcin. Peptide sequences are then used to produce the peptide synthetically and the synthetically produced material has all the uses of the naturally produced material, but may be less expensive to produce.

While we have described and given examples of preferred embodiments of our inventions, it will be apparent to those skilled in the art that changes and modifications may be made without departing from our inventions in their broader aspects. We therefore intend the appended claims to cover all such changes and modifications as fall within the true spirit and scope of our inventions.

We claim:

1. A composition useful for inhibiting the growth of gram-negative bacteria, said composition consisting essentially of a peptide produced by *Propionibacterium shermanii*, the peptide being of molecular weight between 300 daltons and 1200 daltons and comprising the amino acids metbiotite and valine and having an activity of inhibiting the growth of gram-negative bacteria.

2. The composition of claim 1 wherein the peptide further comprises the amino acid glycine.

3. A method for inhibiting the growth of gram-negative bacteria in vitro comprising contacting the bacteria with the composition of claim 1.

4. A method of inhibiting the spoilage of food, the method comprising adding to the food a sufficient amount of the composition of claim 1.

5. A peptide isolated from *Propionibacterium shermanii*, the peptide being of molecular weight between 800 and 1200 daltons and comprising the amino acids metbiotite, valine and glycine, and being inhibitory to the growth of gram-negative bacteria.

6. A method of inhibiting the spoilage of food by gram-negative bacteria, the method comprising adding to the food a sufficient amount of the peptide of claim 5.

7. A composition having an activity of inhibiting the growth of gram-negative bacteria, said composition consisting essentially of a peptide produced by *Propionibacterium shermanii*, the peptide being of molecular weight between 800 and 1200 daltons and comprising the amino acids methionine, valine.

8. The composition of claim 7 wherein the peptide further comprises the amino acid glycine.

9. The composition of claim 8 wherein the activity of inhibiting the growth of gram-negative bacteria is sensitive to alpha-chymotrypsin, pepsin and papain.

10. The composition of claim 9 wherein the activity of inhibiting the growth of gram-negative bacteria is not sensitive to trypsin or catalase.

* * * * *